United States Patent
Kuchitsu et al.

(10) Patent No.: US 9,739,767 B2
(45) Date of Patent: Aug. 22, 2017

(54) METHOD OF SCREENING FOR PLANT DEFENSE ACTIVATORS, PLANT DEFENSE ACTIVATORS, AND METHOD OF ENHANCING IMMUNE RESPONSE

(75) Inventors: Kazuyuki Kuchitsu, Tokyo (JP); Takamitsu Kurusu, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 452 days.

(21) Appl. No.: 13/819,676

(22) PCT Filed: Aug. 10, 2011

(86) PCT No.: PCT/JP2011/068585
§ 371 (c)(1),
(2), (4) Date: Feb. 27, 2013

(87) PCT Pub. No.: WO2012/029539
PCT Pub. Date: Mar. 8, 2012

(65) Prior Publication Data
US 2015/0141252 A1    May 21, 2015

Related U.S. Application Data

(60) Provisional application No. 61/378,403, filed on Aug. 31, 2010.

(51) Int. Cl.
*G01N 33/50* (2006.01)
*C12Q 1/68* (2006.01)
*A01N 43/60* (2006.01)
*A01N 43/90* (2006.01)
*A01N 43/84* (2006.01)
*A01N 43/20* (2006.01)

(52) U.S. Cl.
CPC ......... *G01N 33/5097* (2013.01); *A01N 43/20* (2013.01); *A01N 43/60* (2013.01); *A01N 43/84* (2013.01); *A01N 43/90* (2013.01); *C12Q 1/686* (2013.01); *C12Q 1/6895* (2013.01); *C12Q 2600/136* (2013.01); *C12Q 2600/158* (2013.01); *G01N 2333/415* (2013.01)

(58) Field of Classification Search
CPC ..... G01N 33/5097; G01N 33/50; A01N 43/20
See application file for complete search history.

(56) References Cited

U.S. PATENT DOCUMENTS

2007/0265164 A1*  11/2007  Bartsch et al. ............... 504/105

FOREIGN PATENT DOCUMENTS

| JP | 2006137703 A |   | 6/2006 |   |   |
|---|---|---|---|---|---|
| JP | 2007302634 A | * | 11/2007 |   |   |
| JP | 2007302634 A |   | 11/2007 |   |   |
| JP | 2008-506398 A |   | 3/2008 |   |   |
| WO | WO 9424295 A1 | * | 10/1994 | ........... | C07K 14/415 |
| WO | WO-2006007981 A1 |   | 1/2006 |   |   |
| WO | WO-2006011788 A1 |   | 2/2006 |   |   |
| WO | WO 2010011871 A2 | * | 1/2010 | ............. | A01N 37/44 |

OTHER PUBLICATIONS

Arie et al., Machine Translation, JP2007-302634A, published Nov. 22, 2007, 1-15.*
Hellwig et al., Plant Cell Cultures for the Production of Recombinant Proteins, Review, Nature Biotechnology, 2004, 22(11), 1415-1422.*
Seo et al., Translated Excerpts, Antagonistic Relationship of Salicylic Acid and Jasmonic Acid as Signal Molecules in Resistance to Pathogen Attack and Wounding, Chemical Regulation of Plants, 1997, 32, 37-48.*
Brotman et al., Synthetic Ultrashort Cationic Lipopeptides Induce Systemic Plant Defense Responses Against Bacterial and Fungal Pathogens, Applied and Environmental Microbiology, 2009, 75(16), 5373-5379.*
Yasuda et al., N-Cyanomethyl-2-chloroisonicotinamide Induces Systemic Acquired Resistance in Arabidopsis Without Salicylic Acid Accumulation, Bioscience, Biotechnology and Biochemistry, 2003, 67(2), 322-328.*
Rad et al., Evaluation of Natural and Synthetic Stimulants of Plant Immunity by Microarray Technology, New Phytologist, 2005, 165, 191-202.*
Turner et al., The Jasmonate Signal Pathway, The Plant Cell, 2002, S153-S164.*
Jones et al., The Plant Immune System, Nature Reviews, 2006, 444(16), 323-329.*
Saito et al., Peroxynitrite Generation and Tyrosine Nitration in Defense Responses in Tobacco BY-2 Cells, Plant Cell Physiol., 2006, 47(6), 689-697.*
Derevnina et al., Nine Things to Know About Elicitins, New Phytologist, 2016, 212, 888-895.*
Nakashita et al., "Role of Phytohormones in Systemically Induced Disease Resistance," *Regulation of Plant Growth & Development*, 39(2):203-213 (2004).

(Continued)

*Primary Examiner* — Amy M Bunker
(74) *Attorney, Agent, or Firm* — Marshall, Gerstein & Borun LLP

(57) ABSTRACT

A method of screening for a plant defense activator, which enhances an immune response of a plant, from at least one candidate substance includes: contacting a plant cell in which a jasmonic acid-dependent defense pathway and a salicylic acid-dependent defense pathway of a plant defense system are capable of working independently from each other, with a candidate substance; contacting the plant cell with a trigger material that induces an immune response; and assaying the plant cell after contacting with the trigger material based on an index representing an immune response, to select a target substance that enhances an immune response of the plant. A method of enhancing an immune response of a plant includes use of a specific compound, and a plant immune response enhancer includes the specific compound.

5 Claims, 3 Drawing Sheets

(56) References Cited

OTHER PUBLICATIONS

Seo et al., "Antagonistic Relationship of Salicylic Acid and Jasmonic Acid as Signal Molecules in Resistance to Pathogen Attached and Wounding," *Chemical Regulation of Plants*, 32:37-48 (1997).
International Search Report for Application No. PCT/JP2011/068585, dated Nov. 1, 2011.
Office action issued in Japanese Application No. 2013-510162, mailed Aug. 11, 2015 (English translation).
Bhattacharya et al., "Insight to structural subsite recognition in plant thiol protease-inhibitor complexes: Understanding the basis of differential inhibition and the role of water," *BMC Structural Biology*, http//www.biomedcentral.com/1472-6807/1/4, (2001).
Klausner et al., "BrefeldinA: Insights into the Control of Membrane Traffic and Organelle Structure," *J. Cell Biol.*, 116:1071-1080 (1992).
Nagata et al., "Tobacco BY-2 Cell Line as the "HeLa" Cell in the Cell Biology of Higher Plants," *Intl. Rev. of Cytology*, 132:1-30 (1992).
Vermeer et al., "Visualization of PtdIns3P dynamics in living plant cells," *The Plant Journal*, 47:687-700 (2006).
Written Opinion for PCT/JP2011/068585 dated Nov. 1, 2011.
International Preliminary Report on Patentability for PCT/JP2011/068585 dated Aug. 2, 2011.

\* cited by examiner

Possible function as defense activator in many plant species

~A unique feature of our selective compounds~
Dual activation of SA and JA signaling *in planta*

~Possible function as defense activator in many plant species

~Increment of disease resistance against a variety of pathogen attacks

METHOD OF SCREENING FOR PLANT DEFENSE ACTIVATORS, PLANT DEFENSE ACTIVATORS, AND METHOD OF ENHANCING IMMUNE RESPONSE

TECHNICAL FIELD

The present invention relates to a method of screening for a plant defense activator.

BACKGROUND ART

Similarly to animals, some plants have immunity that provides defense against infection of pathogens. However, the mechanism of plant infection is quite different from that of higher vertebrates; for example, plants do not have phagocytic cells. In an exemplary plant immune system, when a part of a plant is infected, the plant induces localized responses such that cells at the site of infection undergo rapid programmed cell death to prevent the spread of the disease to other parts.

The plant immunity or defense system against infection has two main pathways, one of which is dependent on salicylic acid (hereinafter referred to as "salicylic acid-dependent defense pathway") and the other of which is dependent on jasmonic acid (hereinafter referred to as "jasmonic acid-dependent defense pathway"). Infection of a biotrophic pathogen increases the amount of salicylic acid (SA) in the infected cell, which results in enhanced expression of pathogenesis related (PR) proteins PR-1, PR-2, and PR-5, which, in turn, results in increased expression of acidic PR proteins and induction of systemic acquired resistance (SAR). Probenazole (PBZ) and benzothiadiazole (BTH) are thought to be related to the salicylic acid-dependent defense pathway. Infection of necrotrophic pathogen or wounding increases the amounts of jasmonic acid (JA) and ethylene (ET), which results in enhanced expression of plant defensin genes such as PDF1.2, which, in turn, results in increased expression of basic PR proteins. It has been believed that salicylic acid and jasmonic acid act antagonistically with each other, and that activation of one of the salicylic acid-dependent defense pathway or the jasmonic acid-dependent defense pathway deactivates the other pathway.

Substances that affect plant immunity have a potential of being used as an alternative to pesticides, and are less hazardous to the environment. For example, Japanese Patent Application Laid-open (JP-A) No. 2006-137703 discloses a plant immunity inducing substance obtained by fermentation of leaves of a Poaceae plant using a microorganism belonging to the genus *Bacillus*. Further, an example of a technique of enhancing the resistance of a plant itself is a method disclosed in international publication WO2006/011788, which is a method of increasing the resistance of a plant against pathogenic organisms comprising providing a gene construct including a DNA sequence encoding a receptor for a systemic signal compound of salicylic acid, jasmonic acid, and/or brassinosteroid.

DISCLOSURE OF INVENTION

However, candidate substances as such are directly applied to the entire (intact) plant body in conventional methods of screening candidate substances. Such screening methods take a lot of time, and are burdensome, and the accuracy is not satisfactory in some cases.

In view of the above, an object of the present invention is provision of an accurate and simple method of screening for a plant defense activator, which enhances an immune response of a plant, in a short time.

Aspects of the invention provide the following screening methods and methods of enhancing an immune response of a plant.

[1] A method of screening for a plant defense activator, which enhances an immune response of a plant, from at least one candidate substance, the method comprising:
contacting a plant cell in which a jasmonic acid-dependent defense pathway and a salicylic acid-dependent defense pathway of a plant defense system are capable of working independently from each other, with a candidate substance;
contacting the plant cell with a trigger material that induces an immune response; and
assaying the plant cell after contacting with the trigger material based on an index representing an immune response, to select a target substance that enhances an immune response of the plant.

[2] The screening method according to [1], wherein the plant cell produces no salicylic acid or produces an amount of salicylic acid insufficient for inhibiting the jasmonic acid-dependent defense pathway when the immune response is induced.

[3] The screening method according to [1] or [2], wherein the plant cell is a tobacco BY-2 cell.

[4] The screening method according to any one of [1] to [3], wherein the trigger material is at least one biological elicitor selected from the group consisting of a viable microbe, a microbe-derived material, and a toxin.

[5] The screening method according to any one of [1] to [4], wherein the trigger material comprises at least one selected from the group consisting of a microbe extract, a molecular pattern, and an elicitin.

[6] The screening method according to any one of [1] to [5], wherein the trigger material is cryptogein.

[7] The screening method according to any one of [1] to [6], wherein the index is at least one selected from the group consisting of a salicylic acid selective response index, a jasmonic acid selective response index, and a salicylic-acid/jasmonic-acid non-selective response index.

[8] The screening method according to any one of [1] to [7], wherein the index comprises a salicylic-acid/jasmonic-acid non-selective response index, and the salicylic-acid/jasmonic-acid non-selective response index is a ROS (Reactive Oxygen Species) level within the plant cell.

[9] The screening method according to any one of [1] to [8], wherein the index comprises a salicylic acid selective response index, and the salicylic acid selective response index is an expression level of a PR-1 gene.

[10] The screening method according to any one of [1] to [9], wherein the index comprises a jasmonic acid selective response index, and the jasmonic acid selective response index is an expression level of at least one gene selected from the group consisting of a PDF1.2 gene, a PR-4 gene, a PR-1b gene, and a VSP2 gene.

[11] The screening method according to any one of [1] to [10], wherein the assaying comprises at least two assays based on at least two indices selected from the group consisting of a jasmonic acid selective response index, a salicylic acid selective response index, and a salicylic-acid/jasmonic-acid non-selective response index.

[12] The screening method according to [11], wherein the assaying comprises:
assaying the plant cell after contacting with the trigger material based on a salicylic-acid/jasmonic-acid non-selective response index, to identify a primary candidate substance that activates at least one of the salicylic acid-dependent defense pathway or the jasmonic acid-dependent defense pathway; and subjecting the primary candidate substance to at least one assay using at least one index selected from the group consisting of a jasmonic acid selective response index and a salicylic acid selective response index, to identify a target substance that activates the jasmonic acid-dependent defense pathway or a target substance that activates the salicylic acid-dependent defense pathway.

[13] The screening method according to [11], wherein the assaying comprises:

assaying the plant cell after contacting with the trigger material based on either of a salicylic acid selective response index or a jasmonic acid selective response index, to identify a primary candidate substance that activates the salicylic acid-dependent defense pathway or the jasmonic acid-dependent defense pathway determined by the index used; and subjecting the primary candidate substance to an assay using the other of a salicylic acid selective response index or a jasmonic acid selective response index, to identify a target substance that activates the other pathway determined by the index used.

[14] The screening method according to [11] or [12], wherein the assaying comprises:

assaying the plant cell after contacting with the trigger material based on a salicylic-acid/jasmonic-acid non-selective response index, to identify a primary candidate substance that activates at least one of the salicylic acid-dependent defense pathway or the jasmonic acid-dependent defense pathway;

subjecting the primary candidate substance to an assay based on either of a salicylic acid selective response index or a jasmonic acid selective response index, to identify a secondary candidate substance that activates the salicylic acid-dependent defense pathway or the jasmonic acid-dependent defense pathway determined by the index used; and subjecting the secondary candidate substance to an assay based on the other of a salicylic acid selective response index or a jasmonic acid selective response index, to identify a target substance that activates the other pathway determined by the index used.

[15] A method of enhancing an immune response of a plant, comprising treating a plant material with a liquid formulation including at least one of the following compounds 1 to 5 or a solid formulation including at least one of the following compounds 1 to 5:

Compound 1

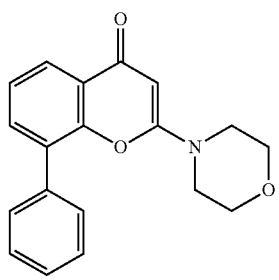

Compound 2

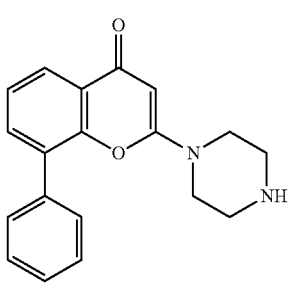

-continued

Compound 3

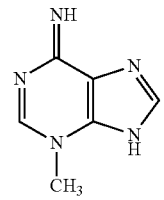

Compound 4

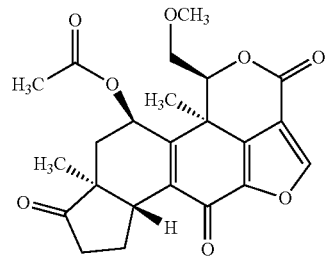

Compound 5

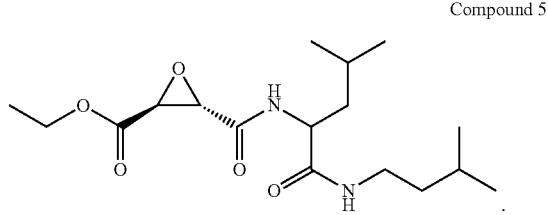

[16] A plant immune response enhancer comprising at least one of the compounds 1 to 5 shown above.

DETAILED DESCRIPTION

Figure 1:
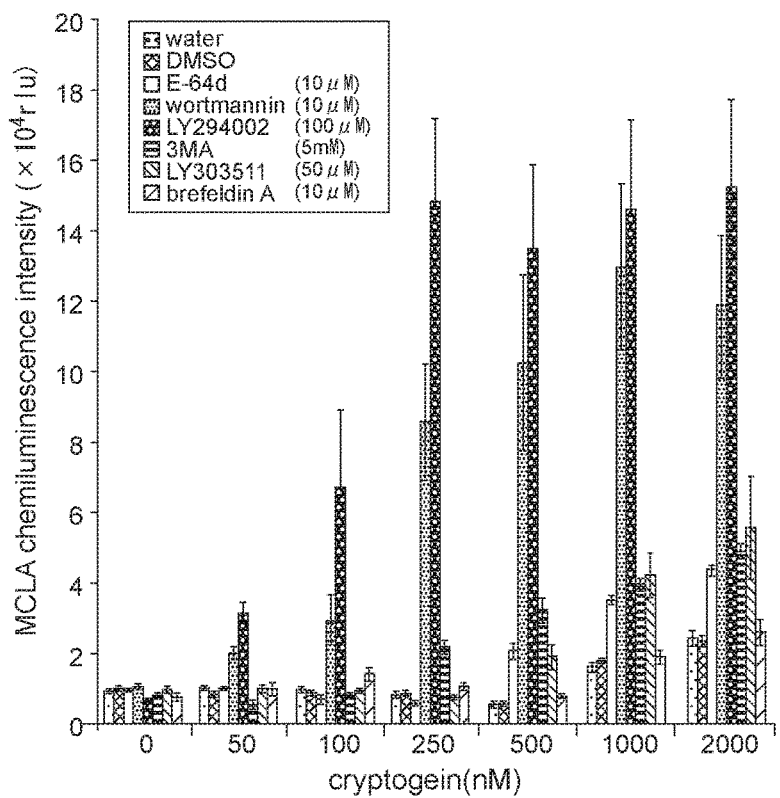
FIG. 1 is a diagram illustrating the effect of test compounds on plant defense response in tobacco BY-2 cells.

The method of screening for a plant defense activator according to the invention is a method of screening for a plant defense activator which enhances an immune response of a plant from at least one candidate substance, and the method includes:

contacting a plant cell in which a jasmonic acid-dependent defense pathway and a salicylic acid-dependent defense pathway of a plant defense system are capable of working independently from each other, with a candidate substance;

contacting the plant cell with a trigger material that induces an immune response; and assaying the plant cell after contacting with the trigger material based on an index representing an immune response, to select a target substance that enhances an immune response of the plant.

According to the invention, a plant cell in which a jasmonic acid-dependent defense pathway and a salicylic acid-dependent defense pathway of a plant defense system do not act antagonistically with each other, and a candidate substance are contacted with each other, and thereafter the plant cell and a trigger material are contacted with each other, and a target substance is selected based on a predetermined index. Therefore, it is not necessary to carry out screening candidate substances by directly using the entire plant body, and a plant defense activator which enhances an immune response of a plant can be obtained by screening in a short time with high accuracy in a simple manner. Further, since a plant cell in which the jasmonic acid-dependent defense pathway and the salicylic acid-dependent defense pathway work without antagonism therebetween is used, it is possible to screen for a plant defense activator that acts on one of the jasmonic acid-dependent defense pathway or the salicylic acid-dependent defense pathway. Furthermore, according to the method, potent substances that cannot be isolated by conventional screening techniques can be isolated.

The mechanism is further explained below. Specifically, in plant cells in general, the salicylic acid-dependent defense pathway and the jasmonic acid-dependent defense pathway act antagonistically with each other, as described above. It is presumed that, for example, the salicylic acid-dependent defense pathway masks the jasmonic acid-dependent defense pathway. Therefore, a substance that enhances the jasmonic acid-dependent defense pathway has not been found by a method which uses a general plant. In contrast, in the present invention, a plant cell having characteristics such that the jasmonic acid-dependent defense pathway and the salicylic acid-dependent defense pathway work independently without antagonism therebetween is used for screening, the masking does not occur, and a plant defense activator that has not been found so far, such as a substance that acts on the jasmonic acid-dependent defense pathway, can be found.

As used herein, plant's defense against infection refers to a self-defense mechanism of a plant against a disease caused by a pathogen, and the self-defense mechanism inhibits infection and proliferation of the pathogen when the plant contacts the pathogen. The specifics of the self-defense mechanism are described in Hideo Nakashita et al., *Regulation of Plant Growth & Development,* 39(2) pp. 203-213 (2004), which is incorporated herein by reference. As used herein, an "immune response" of a plant is a generic term that encompasses responses that contribute to or are involved in the self-defense mechanism of a plant. As used herein, enhancement of an immune response refers to enhancement in the degree (intensity), duration, or the like of an immune response. Therefore, enhancement of an immune response is not limited to a stronger immune response observed at a particular time point, and also encompasses a case in which an immune response lasts for a longer time.

The present invention also provides a novel use of a plant cell in which a jasmonic acid-dependent defense pathway and a salicylic acid-dependent defense pathway of a plant defense system are capable of working independently from each other, which is a use in a novel method of screening for a substance that enhances an immune response of a plant.

Further, according to the invention, a method of enhancing an immune response of a plant is provided which includes treating a plant cell with a liquid formulation including at least one of the compounds 1 to 5 shown above or a solid formulation including at least one of the compounds 1 to 5 shown above. According to this method, a defense power of a plant can be increased in a simple manner.

The term "step" or "process" used herein includes not only a discrete step or process, but also steps or processes which cannot be clearly distinguished from another step or process, as long as the expected effect of the pertinent step or process can be achieved.

In addition, ranges indicated herein with "to" include the numerical values before and after "to".

The invention will be described below.

The screening method according to the invention is a method of screening for a plant defense activator which enhances an immune response of a plant, from at least one candidate substance. The method includes contacting a plant cell in which a jasmonic acid-dependent defense pathway and a salicylic acid-dependent defense pathway of a plant defense system are capable of working independently from each other, with a candidate substance (hereinafter referred to as "pre-treatment step");

contacting the plant cell with a trigger material that induces an immune response (hereinafter referred to as "induction treatment step"); and assaying the plant cell after contacting with the trigger material based on an index representing an immune response, to select a target substance that enhances an immune response of the plant (hereinafter referred to as "screening step").

As used herein, the plant cell in which a jasmonic acid-dependent defense pathway and a salicylic acid-dependent defense pathway of a plant defense system are capable of working independently from each other refers to a plant cell in which the jasmonic acid-dependent defense pathway and the salicylic acid-dependent defense pathway cannot sufficiently maintain a mutual antagonistic state therebetween. Examples of such a plant cell include a plant cell that cannot produce a sufficient amount of salicylic acid or jasmonic acid for inhibiting the effect of the other one of salicylic acid or jasmonic acid due to a mutation or the like of the synthetic pathway(s) of at least one of salicylic acid or jasmonic acid to be produced in response to an external stimulus that induces an immune response, and a plant cell in which the effect of salicylic acid or jasmonic acid, which is supposed to be exerted in response to the external stimulus is inhibited due to the presence or enhancement of a synthetic system of a substance that acts in an inhibitory manner against the synthetic pathway of salicylic acid or jasmonic acid.

The plant cell in which a jasmonic acid-dependent defense pathway and a salicylic acid-dependent defense pathway of a plant defense system are capable of working independently from each other is herein referred to as "plant cell for primary screening" for simplicity.

In the invention, the plant cell for primary screening is preferably a plant cell that produces no salicylic acid or produces an amount of salicylic acid insufficient for inhibiting the jasmonic acid-dependent defense pathway when the immune response is induced, from the viewpoints of simplicity and making it possible to screen for a plant defense activator that can act on the jasmonic acid-dependent defense pathway.

The salicylic acid-dependent defense pathway activity in such a plant cell for primary screening is lower than the salicylic acid-dependent defense pathway activity in general plant cells of the same taxonomic species. The salicylic acid-dependent defense pathway activity may be determined by the level of salicylic acid synthesis, or, alternatively, the expression level of a gene belonging to a salicylic acid-dependent defense pathway.

Examples of the plant cell for primary screening include a tobacco BY-2 cell, a plant cell to which a NahG (salicylic acid hydroxylase) gene has been introduced, a plant cell in which a salicylic acid biosynthesis-related gene has been partially or completely deleted or modified to decrease the activity thereof, and a plant cell in which the activity of salicylic acid-dependent signal transduction system is decreased. In each case, the plant cell for primary screening may be a cultured plant cell. NahG gene is derived from a bacterium (*Pseudomonas* fluorescence) that decomposes salicylic acid into catechol. The plant cell for primary screening is preferably a tobacco BY-2 cell. In BY-2 cells, the amount of salicylic acid synthesized when an immune response is induced is insufficient for inhibiting the activity of the jasmonic acid-dependent defense pathway, and the activity of the salicylic acid-dependent defense pathway is lower than that in other normal tobacco plants, as a result of which the salicylic acid-dependent defense pathway and the jasmonic acid-dependent defense pathway act independently of each other in BY-2 cells. Tobacco BY-2 cell is detailed in Nagata T, Nemoto Y, Hasezawa S, "Tobacco BY-2 cell line as the "HeLa" cell in the cell biology of higher plants", *International Review of Cytology* 132 (1992), 1-30, which is incorporated herein by reference.

When the salicylic acid accumulation levels of the plant cell for use in the present screening method and a general plant cell of the same species are measured without treatment with an elicitor, the salicylic acid accumulation level of the plant cell for use in the screening method is preferably less than half, more preferably less than ⅕, and still more preferably less than 1/10, of that of the general plant. When the salicylic acid accumulation levels of the plant cell for use in the screening method and a general plant cell of the same species are measured after treatment with 2,000 nM cryptogein, the salicylic acid accumulation level of the plant cell for use in the screening method is preferably less than half, more preferably less than ⅕, and still more preferably less than 1/10, of that of the general plant.

In the case of tobacco BY-2 cells compared to normal tobacco plant, the salicylic acid accumulation level of untreated tobacco BY-2 cells is from 10 to 20 ng/g (fresh weight), while the salicylic acid accumulation level of untreated tobacco leaves is several hundred ng/g (fresh weight). When treated with 2,000 nM cryptogein, the salicylic acid accumulation level of treated tobacco BY-2 cells increases to a level of approximately from 100 to 150 ng/g (fresh weight), while the salicylic acid accumulation level of treated tobacco leaves increases to, though varying depending on conditions, a level in the range of from several thousand ng/g (fresh weight) to 10,000 ng/g (fresh weight).

The plant cell for primary screening may be a naturally-derived cell or a cultured cell, and is preferably a cultured cell from the viewpoint of ease of handling and realization of uniform screening.

The contact of the plant cell for primary screening and the candidate substance in the pre-treatment step can be carried out by adding the candidate substance to a medium containing the plant cell for primary screening. A commonly used medium that suits the type of plant cell for primary screening is directly applicable as the medium used for culturing the plant cell for primary screening, without particular limitations. Usually-applied culture conditions are directly applicable as conditions for culturing the plant cell for primary screening. In the screening method according to the invention, a candidate substance is preferably added to a culture medium of the plant cell for primary screening, preferably from 10 minutes to 3 days before contacting the trigger material therewith, more preferably from 1.5 hours to 5 hours before contacting the trigger material therewith, and particularly preferably 3 hours before contacting the trigger material therewith. The addition concentration of the candidate compound may be adjusted, as appropriate.

In the induction treatment step, the plant cell for primary screening after contacting with the candidate substance in the pre-treatment step is contacted with an trigger material. In the screening method of the invention, the trigger material that induces an immune response (sometimes referred to as "immune-response-inducing trigger material" in the specification) may be any substance that induces an immune response in the plant cell for primary screening—in other words, any substance that acts as an elicitor—without particularly limitations. The elicitor may be a non-biological elicitor or a biological elicitor, and is preferably a biological elicitor from the viewpoint of reactivity. Examples of biological elicitors include a viable microbe, a microbe-derived material, and a toxin. These substances may be used singly, or in combination of two or more thereof. Specific examples of substances that act as elicitors include oligosaccharide fragments, glycopeptides, peptides (such as flg22, elf18, and pep13), fatty acids, chitin fragments, ergosterol, lipids (such as lipopolysaccharide and sphingo lipid), and specific proteins (such as xylanase, lipid-transfer proteins (elicitins), harpin, and INF1), each of which may derive from a plant or a pathogenic microbe.

Examples of the viable microbe include a bacterium, a filamentous fungi, a virus, a viroid, a phytoplasma, a nematode, and a protozoan. As used herein, "elicitor" refers to a substance that induces an immune response of a plant. Specific examples thereof include *Magnaporthe grisea*, *Blumeria graminis*, *Golovinomyces orontii*, *Phytophthora infestans*, *Phytophthora parasitica*, *Xanthomonus oryzae* pv. *oryzae*, *Pseudomonas syringae* pv. tomato, *Pseudomonas syringae* pv. *tabaci*, *Rhizoctonia solani*, Tobacco mosaic virus (TMV), *Botrytis cinerea*, and *Alternaria alternata* .

Examples of the microbe-derived material include: an extract derived from any of the above microbes; a molecular pattern such as a PAMP (pathogen-associated molecular pattern), an MAMP (microbe-associated molecular pattern), or a MIMP (microbe-induced molecular pattern); and an elicitin such as cryptogein. Examples of the toxin include Fumonisin B1. The trigger material is preferably cryptogein, which is an elicitin derived from oomycete, *Phytophthora cryptogea* .

In the induction treatment step, the contact of the plant cell for primary screening and the trigger material may be carried out by adding the trigger material to a medium for culturing the plant cell for primary screening. The amount of the trigger material to be added may be an amount necessary for causing an immune response in the plant cell for primary screening, and may be appropriately adjusted in accordance with the type of trigger material to be used, by a person skilled in the art. For example, in a case in which tobacco BY-2 cells are treated with cryptogein, the concentration thereof is preferably from 100 nM to 2,000 nM. An immune response of plant cells can be induced by an elicitor. The immune response may be observed in the form of, for example, cell death, generation of reactive oxygen species (ROS), or expression of defense pathway-related genes.

In the screening step, the plant cell for primary screening after contacting with the trigger material is subjected to an assay based on an index representing an immune response, to select a target substance that enhances an immune response of the plant from candidate substances. The index that indicates an immune response (sometimes referred to as "immune-response index" in the specification) may be any change caused by or associated with an immune response. The index is selected in accordance with the type of target substance to be obtained by screening, and may be at least one selected from the group consisting of a salicylic acid selective response index, a jasmonic acid selective response index, and a salicylic-acid/jasmonic-acid non-selective response index. The salicylic acid selective response index may be employed to determine whether or not the plant exhibits an immune response through the salicylic acid-dependent defense pathway. The jasmonic acid selective response index may be employed to determined whether or not the plant exhibits an immune response through the jasmonic acid-dependent defense pathway. The salicylic-acid/jasmonic-acid non-selective response index is an index other than salicylic acid selective response indices and jasmonic acid selective response indices. The salicylic-acid/jasmonic-acid non-selective response index may be employed to determine whether or not the plant cell exhibits an immune response, without differentiating the salicylic acid-dependent defense pathway and the jasmonic acid-dependent defense pathway from each other.

Examples of the index include ROS (reactive oxygen species) generation or ROS level within a plant cell, the expression level of a salicylic-acid responsive gene (such as an increase in transcription level or generated protein amount), the expression level of a jasmonic-acid responsive gene (such as an increase in transcription level or generated protein amount), cell death, a decrease in an infection rate of a pathogen, the expression level of a defense-related gene (such as an increase in transcription level or generated protein amount), and the accumulation amount of antibacterial substances.

Among these, ROS (reactive oxygen species) generation or a ROS level within a plant cell, cell death, a decrease in an infection rate of a pathogen, an increase of the accumulation amount of antibacterial substances, and the like can preferably be used as a salicylic-acid/jasmonic-acid non-selective response index. In particular, use of a ROS level is more preferable since the use of a ROS level as an index enables the assay to be carried out simply in a short time. In a case in which an increase of the ROS level is employed as the index, the increase in the ROS level is preferably at least 150% relative to an increase in the ROS level observed in a control sample.

Examples of the salicylic-acid responsive gene include PR-1, which may be used as an index that indicates activity of the salicylic acid-dependent defense pathway (which is herein sometimes referred to as "salicylic acid selective response index"). Examples of the jasmonic acid-responsive gene include PDF1.2, PR-4, PR-1b, and VSP2, each of which may be used as an index that indicates activity of the jasmonic acid-dependent defense pathway (which is herein sometimes referred to as "jasmonic acid selective response index").

The time at which the index is assayed is preferably from 10 minutes to 1 day after contacting the trigger material with the plant cell, although this depends on the type of index. When the ROS level (ROS amount) in the cell is employed as the index, the time at which the index is assayed is preferably from 10 minutes to 1 day after contacting the trigger material with the plant cell, more preferably from 3 hours to 7 hours after contacting the trigger material with the plant cell, and still more preferably 5 hours after contacting the trigger material with the plant cell. When the expression level of a salicylic acid-responsive gene or a jasmonic acid-responsive gene is employed as the index, the time at which the index is assayed is preferably from 10 minutes to 1 day after contacting the trigger material with the plant cell, more preferably from 3 hours to 7 hours after contacting the trigger material with the plant cell, and still more preferably 5 hours after contacting the trigger material with the plant cell.

The assay method applied to the index-based assay may be selected, as appropriate, in accordance with the type of index to be employed. For example, in a case in which a ROS level is employed as the index, known methods may be employed such as a method of detecting $.O_2^-$ using chemiluminescence, and a method of detecting hydrogen peroxide ($H_2O_2$) using a chemiluminescent agent such as luminol. In a case in which the expression level of a specific gene is employed as the index, known methods such as a method of detecting the amount of the mRNA of the specific gene using genetic engineering may be applied. When selecting a target substance, a candidate substance that is found to cause a change in the index in the plant cell for primary screening may be selected as a target substance that enhances an immune response, although the selection manner may vary depending on the type of index employed. For example, in a case in which a ROS level is used as the index, a candidate substance that is found to increase the ROS level of the plant cell for primary screening may be selected as a target substance that enhances an immune response. Alternatively, in a case in which a jasmonic acid selective response index or a salicylic acid selective response index is used, a candidate substance that is found to change (increase or decrease) the expression level of the gene corresponding to the index in the plant cell for primary screening may be selected as a target substance that enhances an immune response.

In the case of selecting a target substance that enhances an immune response in the plant regardless of which of the jasmonic acid-dependent defense pathway or the salicylic acid-dependent defense pathway is involved in the enhancement, the screening step may include one-stage selection using a salicylic-acid/jasmonic-acid non-selective response index.

Further, the assay in the screening step in the screening method preferably includes at least two assays based on at least two indices selected from the group consisting of a salicylic acid selective response index, a jasmonic acid selective response index, and a salicylic-acid/jasmonic-acid non-selective response index. Inclusion of at least two assays using at least two different indices in the screening step enables more accurate selection of a target substance that specifically activates either one of the jasmonic acid-dependent defense pathway or the salicylic acid-dependent defense pathway. In a case in which the screening step has two or more stages, the first screening is hereinafter referred to as "primary screening process", the next screening is hereinafter referred to as "secondary screening process", and the subsequent screenings are also referred to in a similar manner.

In a case in which plural assays are carried out based on plural indices, the order of the assays is not limited, and whichever index may be used in the first assay.

The secondary screening process, to which a primary candidate substance selected by the primary screening process is subjected, may further include, prior to carrying out an assay based on an index, the following processes: a pre-treatment process of contacting the primary candidate substance with a plant material; and an induction treatment process of contacting the plant material with a trigger material after the pre-treatment step. The same applies to a case in which three or more screening processes are included.

The plant material used in the pre-treatment step and the induction treatment step in a secondary or subsequent screening process in the multi-stage screening step may belong to the same cell species as or different cell species from the plant cell used as the plant cell for primary screening, and may be a plant cell in which a jasmonic acid-dependent defense pathway and a salicylic acid-dependent defense pathway are capable of working independently from each other, or may be another type of plant cell. The plant material may be, for example, a plant cell, a plant body, a callus, or a seed. A plant material, other than plant cells in which a jasmonic acid-dependent defense pathway and a salicylic acid-dependent defense pathway are capable of working independently from each other, which can be used in a secondary or a subsequent screening process may be a usual plant cell or plant body in which a jasmonic acid-dependent defense pathway and a salicylic acid-dependent defense pathway are antagonistic with each other. The type of plant used as the plant material is not particularly limited, and examples thereof include tobacco (e.g., *Nicotiana tabacum*), Arabidopsis thaliana, and rice (e.g., *Oryza sativa*).

In a case in which the screening method includes plural induction steps, the trigger material used in each induction step may be the same as or different from each other.

The screening step or process in the invention may be selected, as appropriate, in accordance with various properties required for the plant defense activator, which is a target substance to be obtained. The various properties include, for example, the degree of enhancement of plant defense activity, the type and severity of the plant disease which the plant defense activity should deal with, and the selectivity of the defense activation pathway (whether only one of a jasmonic acid-dependent defense pathway or a salicylic acid-dependent defense pathway works or both of a jasmonic acid-dependent defense pathway and a salicylic acid-dependent defense pathway work). Examples of a screening step or process that can be appropriately selected in consideration of these factors include those described below.

The screening step may include:
assaying the plant cell after contacting with the trigger material based on a salicylic-acid/jasmonic-acid non-selective response index, to identify a primary candidate substance that activates at least one of the salicylic acid-dependent defense pathway or the jasmonic acid-dependent defense pathway; and subjecting the primary candidate substance to at least one assay using at least one index selected from the group consisting of a jasmonic acid selective response index and a salicylic acid selective response index, to identify a target substance that activates the jasmonic acid-dependent defense pathway or a target substance that activates the salicylic acid-dependent defense pathway.

In this two-stage screening step, an assay based on a salicylic-acid/jasmonic-acid non-selective response index (dual-responsive index) is carried out in the primary screening process, and thereafter an assay is carried out with respect to a jasmonic acid selective response index or a salicylic acid selective response index in the secondary screening process, the secondary screening process may be carried out only on the primary candidate substance. Therefore, the two-stage screening step enables efficient selection of a target substance by decreasing the number of samples used in the assays.

The screening step may include:
assaying the plant cell for primary screening after contacting with the trigger material based on either of a salicylic acid selective response index or a jasmonic acid selective response index, to identify a primary candidate substance that activates the salicylic acid-dependent defense pathway or the jasmonic acid-dependent defense pathway determined by the index used; and subjecting the primary candidate substance to an assay using the other of a salicylic acid selective response index or a jasmonic acid selective response index, to identify a target substance that activates the other pathway determined by the index used.

In the screening step, the primary screening process and the secondary screening process are carried out based on mutually different indices, as a result of which the number of samples used in the assays is decreased to enable efficient selection of a target substance, and a target substance capable of activating each of the salicylic acid-dependent defense pathway and the jasmonic acid-dependent defense pathway can be selected.

The screening step may include:
assaying the plant cell for primary screening after contacting with the trigger material based on a salicylic-acid/jasmonic-acid non-selective response index, to identify a primary candidate substance that activates at least one of the salicylic acid-dependent defense pathway or the jasmonic acid-dependent defense pathway;

subjecting the primary candidate substance to an assay based on either of a salicylic acid selective response index or a jasmonic acid selective response index, to identify a secondary candidate substance that activates the salicylic acid-dependent defense pathway or the jasmonic acid-dependent defense pathway determined by the index used; and subjecting the secondary candidate substance to an assay based on the other of a salicylic acid selective response index or a jasmonic acid selective response index, to identify a target substance that activates the other pathway determined by the index used.

In this screening step, assays are carried out in the first, second, and third screening processes in which mutually different indices are used. Therefore, the number of samples used in the assays is decreased to enable efficient selection of a target substance, and a target substance capable of activating each of the salicylic acid-dependent defense pathway and the jasmonic acid-dependent defense pathway can surely be selected.

In a case in which a salicylic acid selective response index and a jasmonic acid selective response index are used together in the screening step, the sequence in which the indices are used is not particularly limited.

An example of a screening method including plural screening processes, in which a plant cell producing no salicylic acid or an amount of salicylic acid insufficient for inhibiting the jasmonic acid-dependent defense pathway (hereinafter referred to as "plant cell for primary screening having low salicylic acid activity"; an example is a BY-2 cell) is used is described below. However, the screening method including plural screening processes is not limited thereto, and, for example, a plant material such as a plant body, a seed, a callus, or the like may be employed, instead of the plant cell for primary screening, in the second screening process.

Method A: A method for screening for a substance that activates the jasmonic acid-dependent defense pathway of a plant includes:
- a first screening process including:
  - contacting a first plant cell in which salicylic acid-dependent defense pathway activity is low, with a candidate substance;
  - contacting the first plant cell with a first trigger material that induces an immune response; and
  - assaying the first plant cell with respect to a first index that indicates an immune response,
  - wherein elevation of the first index indicates that the candidate substance is a substance that enhances an immune response, and
- a second screening process including:
  - contacting a second plant cell in which salicylic acid-dependent defense pathway activity is low, with a candidate substance that has been found to enhance an immune response in the first screening process;
  - contacting the second plant cell with a second trigger material that induces an immune response; and
  - assaying the second plant cell with respect to a second index that indicates activity of the jasmonic acid-dependent defense pathway.
  - wherein elevation of the second index indicates that the candidate substance is a substance that activates the jasmonic acid-dependent defense pathway.

Method B: A method for screening for a substance that activates both the jasmonic acid-dependent defense pathway and the salicylic acid-dependent defense pathway of a plant includes:
- a first screening process including:
  - contacting a first plant cell in which salicylic acid-dependent defense pathway activity is low, with a candidate substance;
  - contacting the first plant cell with a first trigger material that induces an immune response; and
  - assaying the first plant cell with respect to a first index that indicates an immune response,
  - wherein elevation of the first index indicates that the candidate substance is a substance that enhances an immune response,
- a second screening process including:
  - contacting a second plant cell in which salicylic acid-dependent defense pathway activity is low, with a candidate substance that has been found to enhance an immune response in the first screening process;
  - contacting the second plant cell with a second trigger material that induces an immune response; and
  - assaying the second plant cell with respect to a second index that indicates activity of the jasmonic acid-dependent defense pathway, and
- a third screening process including:
  - contacting a third plant cell in which salicylic acid-dependent defense pathway activity is low, with the candidate substance that has been found to enhance an immune response in the first screening process;
  - contacting the third plant cell with a third trigger material that induces an immune response; and
  - assaying the third plant cell with respect to a third index that indicates activity of the salicylic acid-dependent defense pathway.
  - wherein elevation of both the second and the third indices indicates that the candidate substance is a substance that activates both the jasmonic acid-dependent defense pathway and the salicylic acid-dependent defense pathway.

Method C: A method for screening for a substance that activates both the jasmonic acid-dependent defense pathway and the salicylic acid-dependent defense pathway of a plant includes:
- a first screening process including:
  - contacting a first plant cell in which salicylic acid-dependent defense pathway activity is low, with a candidate substance;
  - contacting the first plant cell with a first trigger material that induces an immune response; and
  - assaying the first plant cell with respect to a first index that indicates an immune response,
  - wherein elevation of the first index indicates that the candidate substance is a substance that enhances an immune response, and
- a second screening process including:
  - contacting a second plant cell in which salicylic acid-dependent defense pathway activity is low, with a candidate substance that has been found to enhance an immune response in the first screening process;
  - contacting the second plant cell with a second trigger material that induces an immune response; and
  - assaying the second plant cell with respect to a second index that indicates activity of the jasmonic acid-dependent defense pathway and a third index that indicates activity of the salicylic acid-dependent defense pathway
  - wherein elevation of both the second and the third indices indicates that the candidate substance is a substance that activates both the jasmonic acid-dependent defense pathway and the salicylic acid-dependent defense pathway.

In Methods A to C, the first, second, and third plant cells may be the same as each other or different from each other, and the first, second, and third trigger materials may be the same as each other or different from each other. Either of the second plant cell or the third plant cell or each of the second plant cell and the third plant cell may be a general plant cell. The first to third plant cells, the first to third trigger materials, and the first to third indices may be selected from examples of the plant cells, trigger materials, and indices described in the present specification. Many modifications can be made to the Methods A to C. For example, in a case in which the first screening process in Method B serves as the second or third screening process, the second or third screening process may be omitted. In Method B, the second screening process may be conducted before the third screening process, or the third screening process may be conducted before the second screening process.

Other screening methods according to the invention include the following method.

A method of screening for a substance that enhances an immune response of a plant, the method comprising:
- contacting a plant cell in which salicylic acid-dependent defense pathway activity is low, with a candidate substance;
- contacting the plant cell with a trigger material that induces an immune response; and
- assaying the plant cell with respect to an index that indicates an immune response,
- wherein elevation of the index indicates that the candidate substance is a substance that enhances an immune response.

The method of enhancing an immune response of a plant according to the invention includes treating a plant cell with a liquid formulation including at least one of the compounds 1 to 5 shown above or a solid formulation including at least one of the compounds 1 to 5 shown above. Compounds 1 to 5 are compounds of which the efficacy as target substances enhancing an immune response of a plant has been confirmed through the screening method according to the invention. An agent for enhancing an immune response of a plant according to the invention includes at least one of the compounds 1 to 5 as an active substance. A composition according to the invention includes at least one of the compounds 1 to 5, and an agrochemically acceptable carrier. The dosage form of the composition is not particularly limited, and may be a liquid formulation or a solid formulation. The agrochemically acceptable carrier that may be employed to form a liquid formulation or a solid formulation may be a known agrochemically acceptable carrier.

In the method of enhancing an immune response of a plant according to the invention, the plant may be treated with at least one of the compounds 1 to 5 (hereinafter referred to as active component) in any manner, such as atomizing, spreading, spraying, or scattering. When applied, the active component may be in any form such as solution, powder, emulsion, suspension, concentrated liquid preparation, tablet, granule, aerosol, paste, fumigant, or flowable. The active component in any of the above forms may be applied to or incorporated in soil where the plant grow, soil for seeding, paddy field, agricultural water, or water for perfusion.

The formulation to be used for the treatment of the plant may include, in addition to the active compound, an appropriate solid or liquid carrier that is agrochemically acceptable, and, optionally, an adjuvant.

Examples of the solid carrier include botanical materials (such as flour, tobacco stalk powder, soybean powder, walnut-shell powder, vegetable powder, saw dust, bran, bark powder, cellulose powder, and vegetable extract residue), fibrous materials (such as paper, corrugated cardboard, and old rags), artificial plastic powders, clays (such as kaolin, bentonite, and fuller's earth), talc, other inorganic materials (such as pyrophyllite, sericite, pumice, sulfur powder, and active carbon), and chemical fertilizers (such as ammonium sulfate, ammonium phosphate, ammonium nitrate, urea, and ammonium chloride).

Examples of the liquid carrier include water, alcohols (such as methanol and ethanol), ketones (such as acetone and ethyl methyl ketone), ethers (such as diethyl ether, dioxane, cellosolve, and tetrahydrofuran), aromatic hydrocarbons (such as benzene, toluene, xylene, and methylnaphthalene), aliphatic hydrocarbons (such as gasoline, kerosene, and lamp oil), esters, nitriles, acid amides (such as N,N-dimethylformamide and N,N-dimethylacetamide), and halogenated hydrocarbons (such as dichloroethane and carbon tetrachloride).

Examples of the adjuvant include surfactants, spreaders, dispersants, and stabilizers. Examples of surfactants include alkyl sulfates, alkyl sulfonates, alkylaryl sulfonates, polyethyleneglycol ethers, and polyhydric alcohols. Examples of spreaders or dispersants include casein, gelatin, starch powder, carboxymethyl cellulose, gum arabic, alginic acid, lignin, bentonite, molasses, polyvinyl alcohol, pine oil, and agar. Examples of stabilizers include PAP (a mixture of isopropylphosphate), tricresyl phosphate (TCP), tall oil, epoxidized oil, surfactants, and fatty acids and esters thereof.

The content of the active component in the formulation is preferably from 0.1 to 95% by weight, and more preferably from 1.0 to 75% by weight. The formulation may include other agrochemically active ingredients such as fungicides, insecticides, herbicides or fertilizers. When applied to soil, the application amount of the active component is preferably from 1 g to 5 kg per hectare, and more preferably from 10 g to 1.0 kg per hectare. The application may be conducted only once, or plural times, in which case the frequency may be in the range of once a day to once a year, and more preferably from once a week to once a year.

In an exemplary embodiment, the active component may be applied by affusion, or by direct infiltration to leaves. In another exemplary embodiment, efficient treatment is achieved with less labor amount, by diluting the active component with a carrier such as clay mineral, coating plant seeds therewith, and then sowing the seeds. Similarly, it is also possible to treat the seeds with the active component in the form of a liquid formulation or a powder formulation directly before the sowing, and sow the treated seeds In another exemplary embodiment, the active component may be applied to a grown plant by scattering the active component toward the grown plant or contacting the active component with the grown plant, in which case the active component may be in the form of a liquid formulation or a powder formulation. In still another embodiment, the active component may be applied to a grown plant by affusion of a liquid formulation containing the active component into soil, or by blending a powder formulation containing the active component with soil by ploughing.

EXAMPLES

The present invention will be further specifically explained below by way of Examples, but the invention is not limited to the following Examples as far as it is not departed from the gist thereof. Unless otherwise is indicated, "%" is on a mass basis.

A tobacco BY-2 cell was selected as a plant for testing, and was used in the below-described method of screening for a plant defense activator. The following six compounds were used as candidate substances.

Compound 1

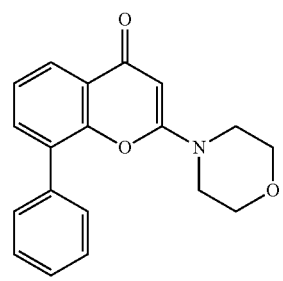

(LY 294002, available from SIGMA).

Compound 2

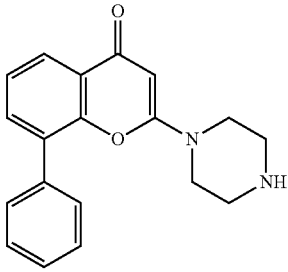

LY 303511
(LY 303511, available from Calbiochem).

-continued

Compound 3

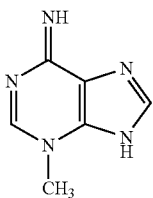

(3MA (e-methyladenine), available from SIGMA).

Compound 4

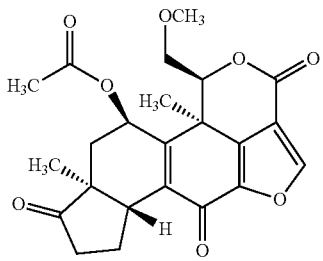

(wortmannin, available from SIGMA).

Compound 5

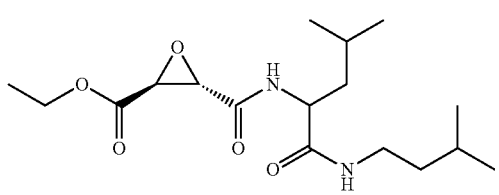

(E-64d, available from PEPTIDE INSTITUTE, INC.)

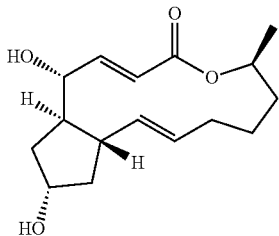

Brefeldin A
(available from Wako Pure Chemical Industries Ltd.).

Tobacco BY-2 cells of three days after subculture were used in this experiment. Chemical compounds were added to the tobacco BY-2 cells 3 h prior to the elicitor (cryptogein) treatment (50-2000 nM). A 125 μl aliquot of cells was collected at the indicated time (5 h) after the elicitor (cryptogein) application and treated with 2 μM MCLA (Molecular Probes, Eugene, Oreg., USA). In order to evaluate ROS generation, the $.O_2$-dependent chemiluminescence was measured with a LUMICOUNTER 2500 (Microtech Nition, Chiba, Japan) with continuous aeration by shaking of the vial. Average values and standard errors of three independent experiments are shown in FIG. 1. In the graph shown in FIG. 1, bars are aligned in the order of water, DMSO, E-64d (Compound 5), wortmannin (Compound 4), LY294002 (Compound 1), 3MA (Compound 3), LY303511 (Compound 2), and brefeldin A from left to right. In FIG. 1, the base line of ROS level was indicated by a horizontal line.

Since the ROS level increases shortly after application of the trigger material, measurement with the ROS level as the index provides a quick and simple way of screening.

Subsequently, the compounds shown above were subjected to assays using various plant materials and using a jasmonic acid selective response index and a salicylic acid selective response index.

RNA Isolation and Real-time RT-PCR Quantification

Total RNA was isolated from plant cells using Trizol (Invitrogen, Carlsbad, Calif., USA) reagent in accordance with the manufacturer's protocol and quantified using a spectrophotometer. First-strand cDNA was synthesized from 3 μg total RNA with an oligo-dT primer and reverse transcriptase.

Real-time PCR was performed using an ABI PRISM 7300 sequence detection system (Applied Biosystems, Foster City, Calif., USA) with SYBR Green real-time PCR Master Mix (TOYOBO, Osaka, Japan) and the gene-specific primers. PCR amplification was performed with an initial denaturation at 95° C. for 10 min followed by 40 cycles of incubations at 95° C. for 15 s, 60° C. for 15 s, and 72° C. for 45 s. Relative mRNA abundances were calculated using the comparative Ct method. Actin or tubulin was used as an internal control. The following primers were used in the experiment.

Primers List

```
Arabidopsis (Arabidopsis thaliana) tubulin
Forward primer
5'-ATTCCCCCGTCTTCACTTCT-3'

Reverse primer
5'-CACATTCAGCATCTGCTCGT-3'

Arabidopsis (Arabidopsis thaliana) PR1
Forward primer
5'-TTCTTCCCTCGAAAGCTCAA-3'

Reverse primer
5'-AAGGCCCACCAGAGTGTATG-3'

Arabidopsis (Arabidopsis thaliana) PDF1.2
Forward primer
5'-TCATGGCTAAGTTTGCTTCC-3'

Reverse primer
5'-AATACACACGATTTAGCACC-3'

Tobacco (Nicotiana tabacum) actin
Forward primer
5'-GGGTTTGCTGGAGATGATGCT-3'

Reverse primer
5'-GCTTCATCACCAACATATGCAT-3'

Tobacco (Nicotiana tabacum) PR1a
Forward primer
5'-GTCCATACTAATTGAAACGACCTAC-3'

Reverse primer
5'-CCACTTCAGAGGATTACATATATAGTAC-3'

Tobacco (Nicotiana tabacum) PR1b
Forward primer
5'-TTTTGGTGGTATTATGGAGGTGTG-3'

Reverse primer
5'-ACAATTAACTGCCGTTGACTCATC-3'

Rice (Oryza sativa) actin
Forward primer
5'-TGCACAGGAAATGCTTCTAATTCTT-3'

Reverse primer
5'-ACGGCGATAACAGCTCCTCTT-3'
```

-continued

```
Rice (Oryza sativa) PBZ1
Forward primer
5'-CGCCGCAAGTCATGTCCTA-3'

Reverse primer
5'-CTTCCCCACCTTGCTTGCTTTCTG-3'

Rice (Oryza sativa) WRKY45
Forward primer
5'-GACACGGGCCGGGTAAA-3'

Reverse primer
5'-TTTCTGTACACACGCGTGGAA-3'
```

The plant materials for RNA extraction were prepared as described below, and the expression of the individual genes was measured.

Arabidopsis seedlings were grown on MS plate for 12 days and then the seedlings were transferred to MS plates containing chemical compounds. After grown for 3 or 6 days, the samples for RNA extraction were collected. The results are shown in FIG. 2.

Figure 4:
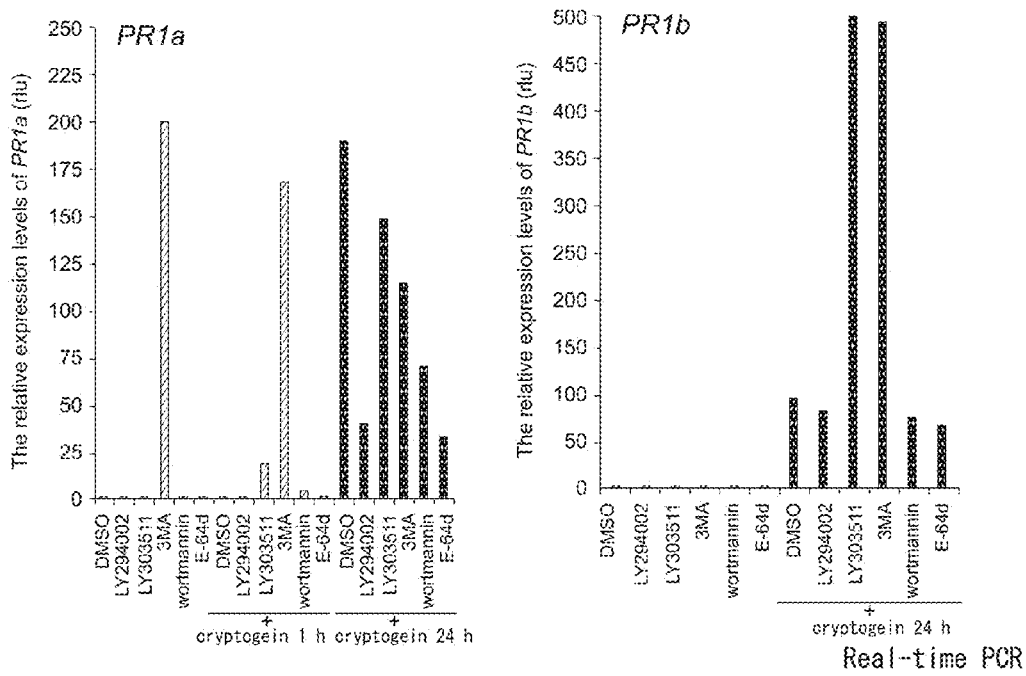
FIG. 4 is a diagram illustrating the effect of test compounds on innate immunity in tobacco plant.

Tobacco seedlings were grown on MS plate for 7 days and then the seedlings were transferred to MS plates containing chemical compounds. After grown for 6 days, cryptogein (2000 nM) was added to the medium and the samples for RNA extraction were collected at the indicated time (0, 1 and 24 h). The results are shown in FIG. 4.

Rice seedlings were grown on water for 5 days and then the seedlings were transferred to water media containing chemical compounds. After grown for 2 days, N-acetylchitoheptaose ([GlcNAc]$_7$) (10 µM) as an elicitor was added to the water media and the samples for RNA extraction were collected at the indicated time (0, 1 and 24 h). The results are shown FIG. 5.

Figure 2:
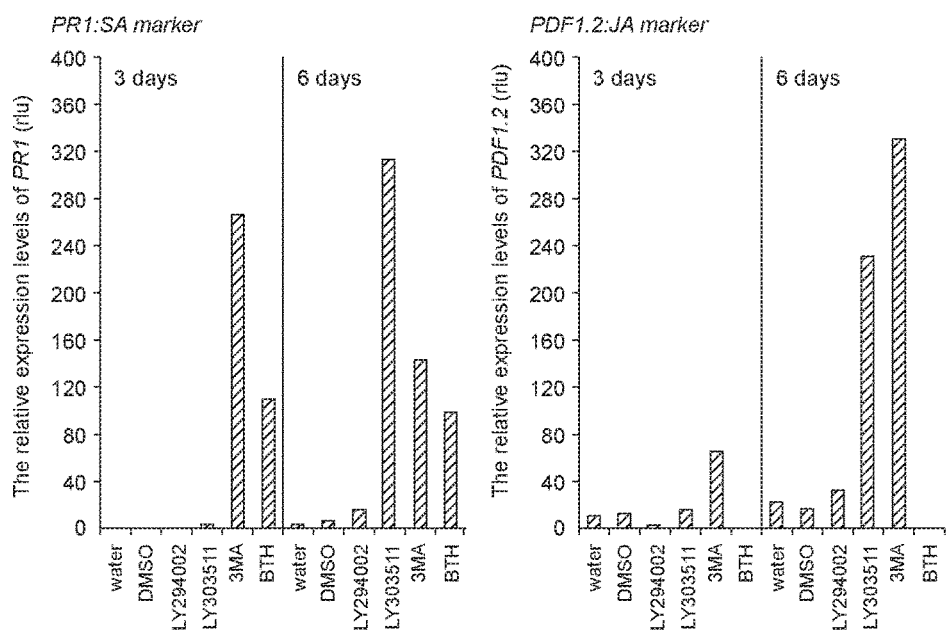
FIG. 2 is a diagram illustrating the effect of test compounds on innate immunity in planta.

FIG. 2 demonstrates that the above compounds 2 and 3 activated both the salicylic acid-dependent defense pathway and the jasmonic acid-dependent defense pathway. The dual activation of salicylic acid and jasmonic acid signaling is a surprising finding, and has been achieved only by the present invention. FIG. 4 demonstrates that the compounds 2 and 3 enhanced an immune response after treatment with cryptogein, and FIG. 5 demonstrates that the compound 3 enhanced an immune response and the enhanced immune response was observed 24 hours after the elicitor application (right bar). The capacity of compounds 1 to 5 for enhancing an immune response of a plant has been discovered for the first time by the screening method of the invention.

Figure 5:
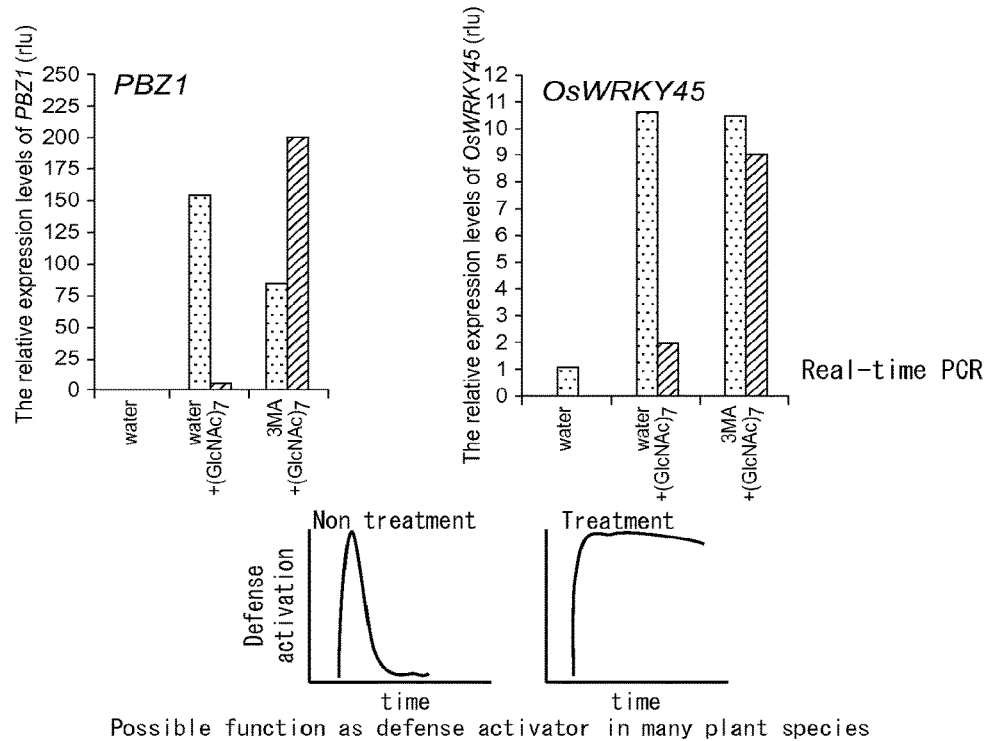
FIG. 5 is a diagram illustrating the effect of test compounds on innate immunity in rice.

In FIG. 5, probenazole (PBZ) and benzothiadiazole (BTH) are major plant defense activators and protect plants from disease by activating the salicylic acid-dependent defense pathway. PBZ1 is probenazole inducible genel (PBZ1)/PR10a and the expression level of PBZ1 is used as a responsive marker in rice innate immunity. OsWRKY45 is a BTH- and salicylic acid-inducible WRKY transcription factor gene in rice that was upregulated within 3 h after BTH treatment. Overexpression of OsWRKY45 markedly enhances resistance to rice blast fungus. In this experiment, we used the expression level of OsWRKY45 as a responsive marker in rice innate immunity as well as the expression level of PBZ1.

Figure 3:
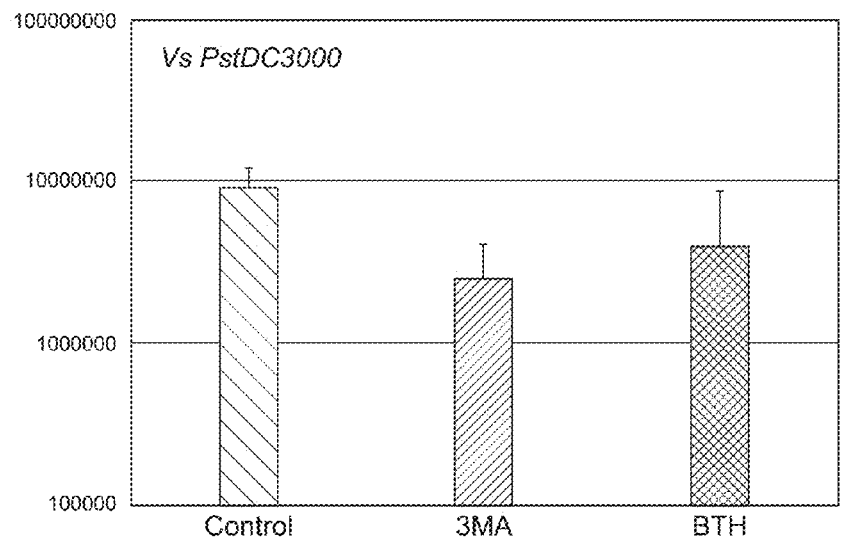
FIG. 3 is a diagram illustrating the effect of test compounds on plant disease resistance.

FIG. 3 shows the effect of selective defense activator candidates on plant disease resistance.

Treatments of Chemical Compounds, Pathogen Infection Assay

Arabidopsis thaliana (Col-0) were grown in sterilized potting soil (Kureha) in plastic pots (5 cm×5 cm×5 cm) inside a growth chamber under a 16 h-8 h light-dark regimen at 22° C. with 60% humidity. After grown for 3 weeks, plants were irrigated with chemical compounds for 5 days.

Pseudomonas syringae pv tomato (Pst) DC3000 was cultured in nutrient broth medium (Eiken Chemical) for 24 h at 28° C., and a bacterial suspension was prepared in 10 mM MgCl$_2$ (2×10$^5$ colony-forming units per mL). Challenge inoculation was performed by dipping the plants in bacterial solution. After incubation for 3 days at 22° C., the leaves were harvested from the inoculated plants. Three to four leaves from different plants were combined, weighed, and then homogenized in 10 mM MgCl$_2$; the homogenate was then plated on nutrient broth agar containing rifampicin (50 mg/L) at appropriate dilutions. After incubation for 2 days at 28° C., the number of rifampicin-resistant bacterial colonies was counted. More than six homogenized samples were prepared for each experiment.

As shown in FIG. 3, the compound 3 is demonstrated to be effective in enhancing resistance to a plant disease.

Figure 6:
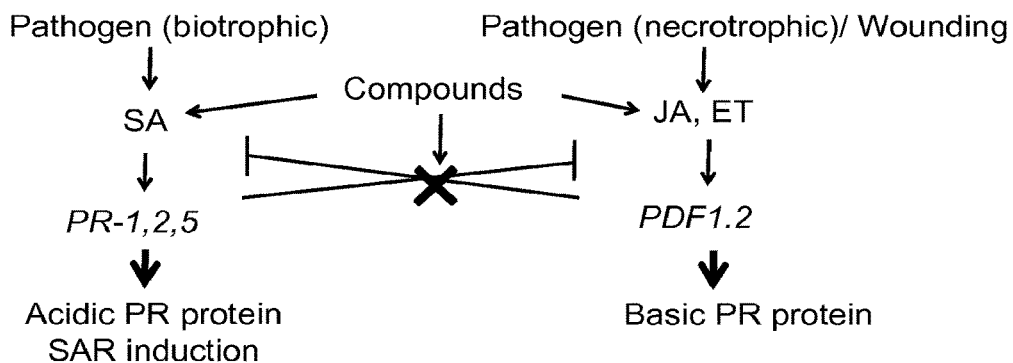
FIG. 6 is a diagram schematically illustrating dual activation of a salicylic acid-dependent defense pathway and a jasmonic acid-dependent defense pathway.

As described above, the salicylic acid-dependent defense pathway and the jasmonic acid-dependent defense pathway are basically dependent from each other, and have been thought to act antagonistically. However, the present invention makes it possible to screen for a compound that activates both the salicylic acid-dependent defense pathway and the jasmonic acid-dependent defense pathway, as schematically shown in FIG. 6. Further, in the case of using an ROS level as the index that represents an immune response, the screening system may employ a high sensitive camera, thereby providing a simultaneous measurement system and enabling high-throughput screening.

The disclosure of U.S. provisional Application No. 61/378,403, which was filed on Aug. 31, 2010, is hereby incorporated by reference in its entirety.

All references, patent applications, and technical standards described in the present specification are herein incorporated in their entirety by reference into the specification, to the same extent as if each individual reference, patent application or technical standard was specifically and individually indicated to be incorporated herein by reference.

The invention claimed is:

1. A method of screening for a plant defense activator, which enhances an immune response of a plant, the method comprising:
   (a) contacting a plant cell with a candidate substance, wherein the plant cell is a cultured tobacco BY-2 cell, wherein the candidate substance is a substance that activates a jasmonic acid-dependent defense pathway;
   (b) contacting the plant cell with a trigger material that induces an immune response, wherein the trigger material is an elicitin, and wherein the trigger material is added to a culture medium for culturing the plant cell, and wherein the candidate substance is added to a culture medium of the plant cell 10 minutes to 3 days before contacting of the plant cell with the trigger material;
   (c) assaying the plant cell after contacting the plant cell with the trigger material using a salicylic acid/jasmonic acid non-selective response index, wherein the salicylic acid/jasmonic acid non-selective response index is reactive oxygen species (ROS) generation or ROS level within a plant cell, and wherein the ROS generation or ROS level within the plant cell is assayed 10 minutes to 1 day after contacting the plant cell with the trigger material;
   (d) selecting the candidate substance as a plant defense activator that activates plant defense via a jasmonic acid-dependent defense pathway when the plant cell that has been contacted with the candidate substance and the trigger material exhibits an immune response that is at least 150% greater relative to the immune response observed in a reference plant cell, wherein the reference plant cell is a cultured tobacco BY-2 cell that has been contacted with the trigger material but not contacted with the candidate substance; and
   (e) treating a plant material with a liquid formulation including the plant defense activator, wherein the plant material exhibits an immune response when challenged with an elicitor, wherein the immune response is at least 150% greater relative to the immune response observed in a reference plant material, wherein the plant material is selected from the group consisting of a plant cell, a plant body, a callus and a seed, wherein the reference plant material is the same plant material that is challenged with the same elicitor but not treated with the liquid formulation including the plant defense activator, and wherein the step of treating the plant material with the liquid formulation is performed by at least one method selected from the group consisting of atomizing, spreading, spraying and scattering.

2. The method of claim 1, wherein the salicylic acid/jasmonic acid non-selective response index representing an immune response is reactive oxygen species (ROS) generation.

3. The method of claim 1, wherein the salicylic acid/jasmonic acid non-selective response index is reactive oxygen species (ROS) level within a plant cell.

4. The method of claim 1, wherein the immune response includes an increase in ROS level within the plant cell that is at least 150% relative to an increase in ROS level observed in the reference plant cell.

5. The method of claim 4 wherein the ROS level is assayed using at least one method selected from the group consisting of detecting superoxide anion radical ($.O^{2-}$) using chemiluminescence, and detecting hydrogen peroxide ($H_2O_2$) using a chemiluminescent agent.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Arabidopsis thaliana

<400> SEQUENCE: 1 attccccgt cttcacttct                                               20
```

```
<210> SEQ ID NO 2
<211> LENGTH: 20
<212> TYPE: DNA
<213> ORGANISM: Arabidopsis thaliana

<400> SEQUENCE: 2
cacattcagc atctgctcgt                                              20

<210> SEQ ID NO 3
<211> LENGTH: 20
<212> TYPE: DNA
<213> ORGANISM: Arabidopsis thaliana

<400> SEQUENCE: 3
ttcttccctc gaaagctcaa                                              20

<210> SEQ ID NO 4
<211> LENGTH: 20
<212> TYPE: DNA
<213> ORGANISM: Arabidopsis thaliana

<400> SEQUENCE: 4
aaggcccacc agagtgtatg                                              20

<210> SEQ ID NO 5
<211> LENGTH: 20
<212> TYPE: DNA
<213> ORGANISM: Arabidopsis thaliana

<400> SEQUENCE: 5
tcatggctaa gtttgcttcc                                              20

<210> SEQ ID NO 6
<211> LENGTH: 20
<212> TYPE: DNA
<213> ORGANISM: Arabidopsis thaliana

<400> SEQUENCE: 6
aatacacacg atttagcacc                                              20

<210> SEQ ID NO 7
<211> LENGTH: 21
<212> TYPE: DNA
<213> ORGANISM: Nicotiana tabacum

<400> SEQUENCE: 7
gggtttgctg gagatgatgc t                                            21

<210> SEQ ID NO 8
<211> LENGTH: 22
<212> TYPE: DNA
<213> ORGANISM: Nicotiana tabacum

<400> SEQUENCE: 8
gcttcatcac caacatatgc at                                           22

<210> SEQ ID NO 9
<211> LENGTH: 25
<212> TYPE: DNA
<213> ORGANISM: Nicotiana tabacum

<400> SEQUENCE: 9
gtccatacta attgaaacga cctac                                        25
```

<210> SEQ ID NO 10
<211> LENGTH: 28
<212> TYPE: DNA
<213> ORGANISM: Nicotiana tabacum

<400> SEQUENCE: 10
ccacttcaga ggattacata tatagtac                                    28

<210> SEQ ID NO 11
<211> LENGTH: 24
<212> TYPE: DNA
<213> ORGANISM: Nicotiana tabacum

<400> SEQUENCE: 11
ttttggtggt attatggagg tgtg                                        24

<210> SEQ ID NO 12
<211> LENGTH: 24
<212> TYPE: DNA
<213> ORGANISM: Nicotiana tabacum

<400> SEQUENCE: 12
acaattaact gccgttgact catc                                        24

<210> SEQ ID NO 13
<211> LENGTH: 25
<212> TYPE: DNA
<213> ORGANISM: Oryza sativa

<400> SEQUENCE: 13
tgcacaggaa atgcttctaa ttctt                                       25

<210> SEQ ID NO 14
<211> LENGTH: 21
<212> TYPE: DNA
<213> ORGANISM: Oryza sativa

<400> SEQUENCE: 14
acggcgataa cagctcctct t                                           21

<210> SEQ ID NO 15
<211> LENGTH: 19
<212> TYPE: DNA
<213> ORGANISM: Oryza sativa

<400> SEQUENCE: 15
cgccgcaagt catgtccta                                              19

<210> SEQ ID NO 16
<211> LENGTH: 24
<212> TYPE: DNA
<213> ORGANISM: Oryza sativa

<400> SEQUENCE: 16 cttcccccacc ttgcttgctt tctg                                       24

<210> SEQ ID NO 17
<211> LENGTH: 17
<212> TYPE: DNA
<213> ORGANISM: Oryza sativa

<400> SEQUENCE: 17

-continued

| gacacgggcc gggtaaa | 17 |

```
<210> SEQ ID NO 18
<211> LENGTH: 21
<212> TYPE: DNA
<213> ORGANISM: Oryza sativa

<400> SEQUENCE: 18
```

| tttctgtaca cacgcgtgga a | 21 |